United States Patent [19]
Dingler et al.

[11] Patent Number: 6,071,299
[45] Date of Patent: Jun. 6, 2000

[54] MEDICAL INSTRUMENT

[75] Inventors: Andreas Dingler, Birkenfeld; Ernst Falk, Sternenfels-Diefenbach, both of Germany

[73] Assignee: Richard Wolf GmbH, Knittlingen, Germany

[21] Appl. No.: 09/293,373

[22] Filed: Apr. 16, 1999

[30] Foreign Application Priority Data

Apr. 16, 1998 [DE] Germany ............... 298 06 799 U

[51] Int. Cl.⁷ .......................................... A61B 17/28
[52] U.S. Cl. ............................................ 606/205
[58] Field of Search ............................. 606/205, 206, 606/207, 208, 209, 210

[56] References Cited

U.S. PATENT DOCUMENTS 5,368,606  11/1994  Marlow et al. ..................... 606/170
5,797,957  11/1994  Palmer et al. ..................... 606/205

FOREIGN PATENT DOCUMENTS 36 01 166   7/1987   Germany.

*Primary Examiner*—Michael Buiz
*Assistant Examiner*—Vy Q. Bui
*Attorney, Agent, or Firm*—Cohen, Pontani, Lieberman & Pavane

[57] ABSTRACT

A medical instrument including a housing, a shank a proximal end and a distal end, the proximal end of the shank being connected to the housing, an openable and closable two-part tool provided at the distal end of the shank, an actuating element that runs through the housing and the shank so as to be axially shiftable for actuating the tool, and an elastic buffer as overload protection whereby the buffer elastically deforms to buffer an axial force overload transmitted from the actuating element onto the shank. The buffer is formed as a shaped body of elastic material arranged between the shank and the housing so that during overloading the buffer is deformed by the shank which at the same time shifts axially proximally with respect to the housing.

6 Claims, 3 Drawing Sheets

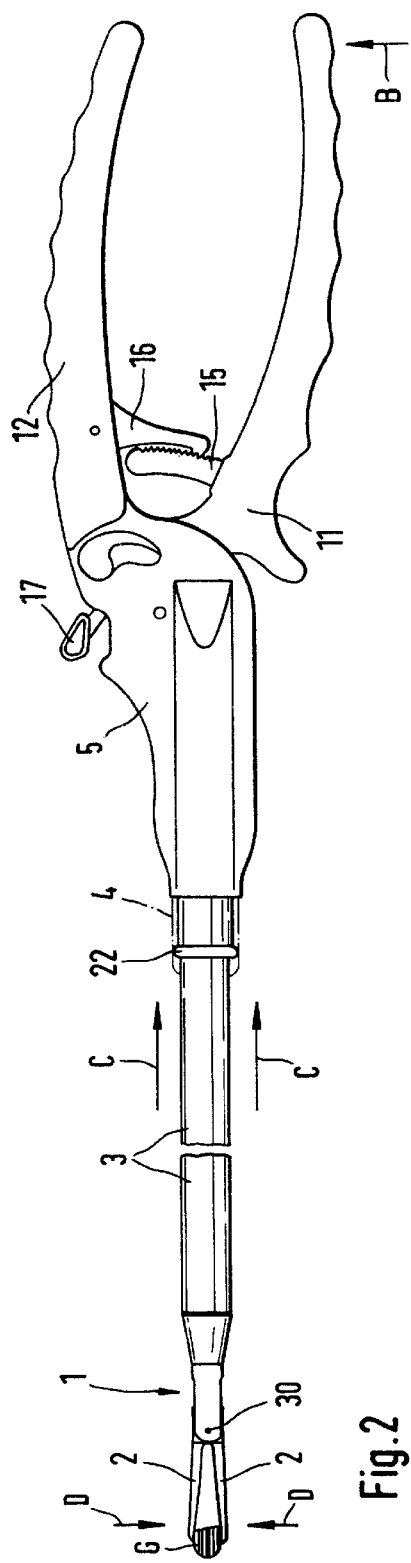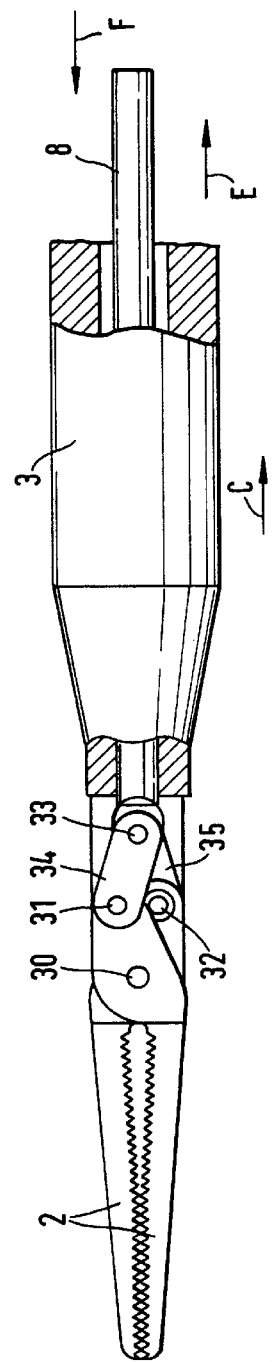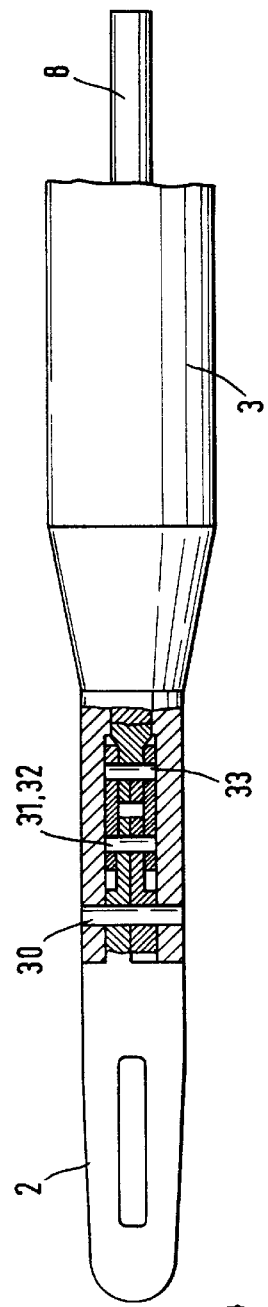

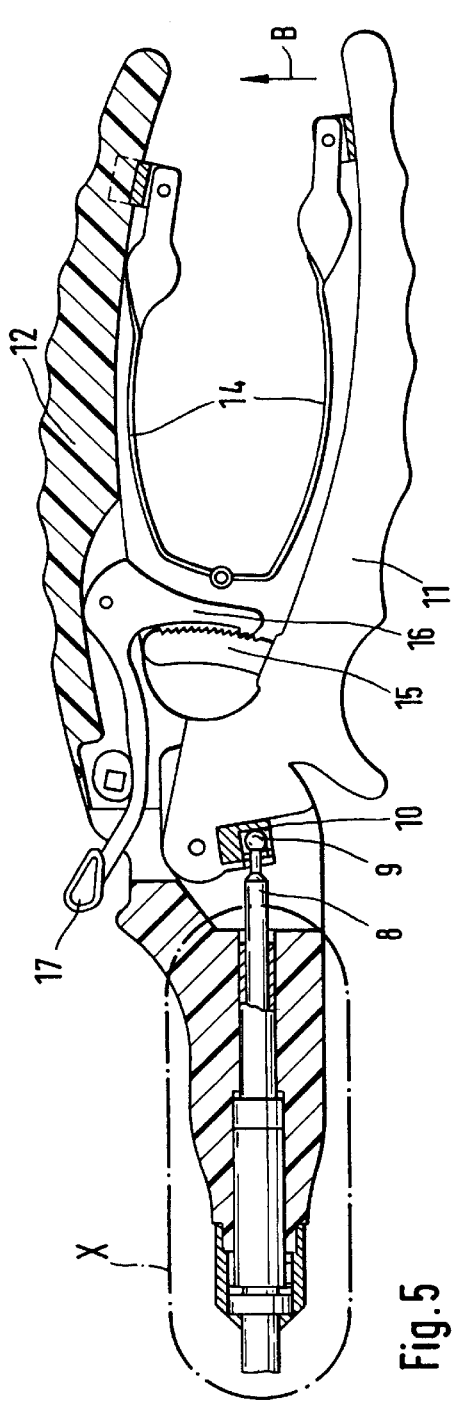
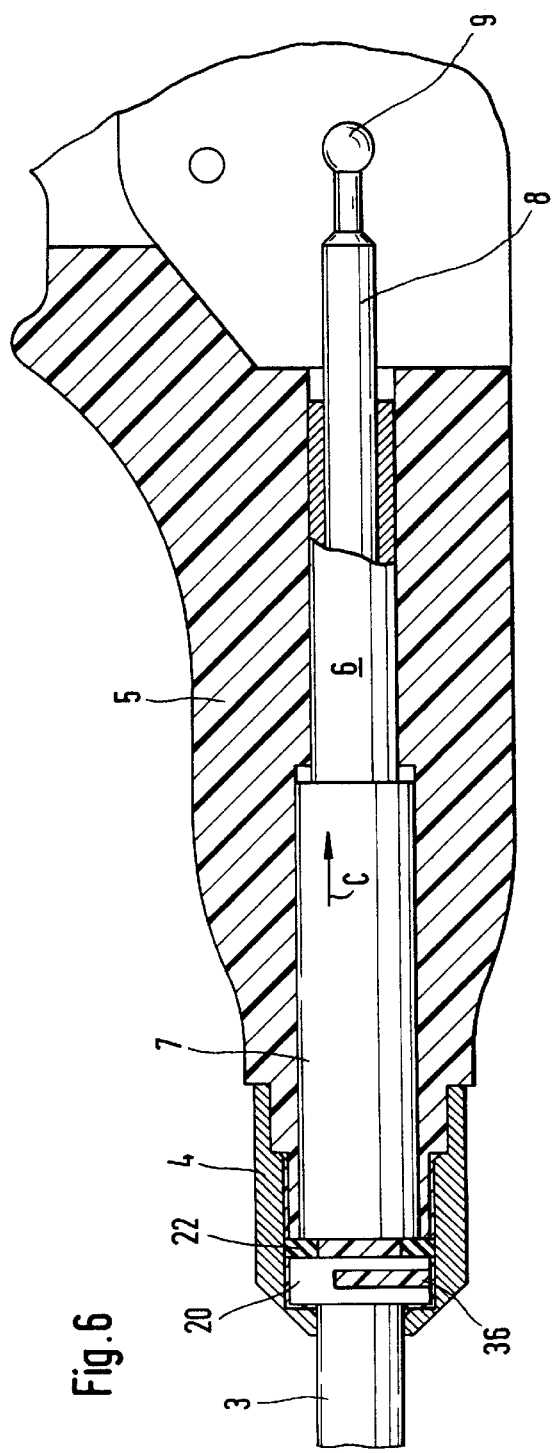
Fig. 5
Fig. 6

MEDICAL INSTRUMENT

BACKGROUND OF THE INVENTION

The invention relates to a medical instrument with a shank, a housing and an openable and closable two part tool which is provided at the distal instrument end and which for closing and opening can be actuated by the axial shifting of an actuating element running through the housing and the shank, and with an elastic buffer as an overload protection which in the case of overloading by way of elastic deformation buffers an axial force transmitted from the actuating element onto the shank.

With such a medical instrument designed as a microsurgical forceps (DE 36 01 166 A1) the flow of force is guided from the grip part to the associated jaw part via a two-part element. This element is held together by the buffer exerting a predetermined elastic pretension in the position in which it transmits the force exerted onto the grip parts onto the jaw parts. If this force exceeds the pretension of the buffer then the element is separated against the effect of the pretensioning. Thus the force transmitted onto the jaw parts may not exceed the value predetermined by the pretension of the buffer and a breakage of the jaw parts is ruled out.

With this instrument the buffer is designed as a metallic helical spring which lies within the instrument housing. On account of this constructional type there results considerable constructional size, a complicated assembly and high manufacturing costs. Furthermore the spring force of the helical spring serving as a buffer may not be simply influenced by way of a directed selection of material.

BRIEF SUMMARY OF THE INVENTION

Accordingly it is the object of the invention to provide a medical instrument of the indicated type with a small constructional size, with a simple and inexpensive manufacture and assembly, with which in a simple manner the force of the buffer decisive for the overload protection may be predetermined by the directed selection of material already at the time of manufacture.

The above object, proceeding from the initially mentioned instrument, is achieved in that the buffer is formed as a shape body of elastic material and is arranged between the shank and the non-moving instrument housing such that in the case of overloading it may be planely deformed by the shank which at the same time shifts axially proximally with respect to the housing.

BRIEF DESCRIPTION OF THE DRAWINGS

Further advantageous embodiment forms and formations of the medical instrument according to the invention are described in more detail by way of the drawing. The drawing figures show individually:

FIG. 2 the same view of the instrument with a closed tool;

FIG. 3 a detailed view of the distal end of the medical instrument of FIG. 2, wherein it can be seen how the forceps jaw parts arc linked on the actuating element and on the shank;

FIG. 4 likewise the distal end of the medical instrument shown in FIG. 2, but in a partly sectioned plan view rotated about 90° with respect to FIG. 3;

FIG. 5 the proximal end of the medical instrument shown in the FIGS. 1 and 2, partly sectioned; and FIG. 6 a sectioned, enlarged detailed view of a region X in FIG. 5.

DETAILED DESCRIPTION OF THE INVENTION

Figure 1:
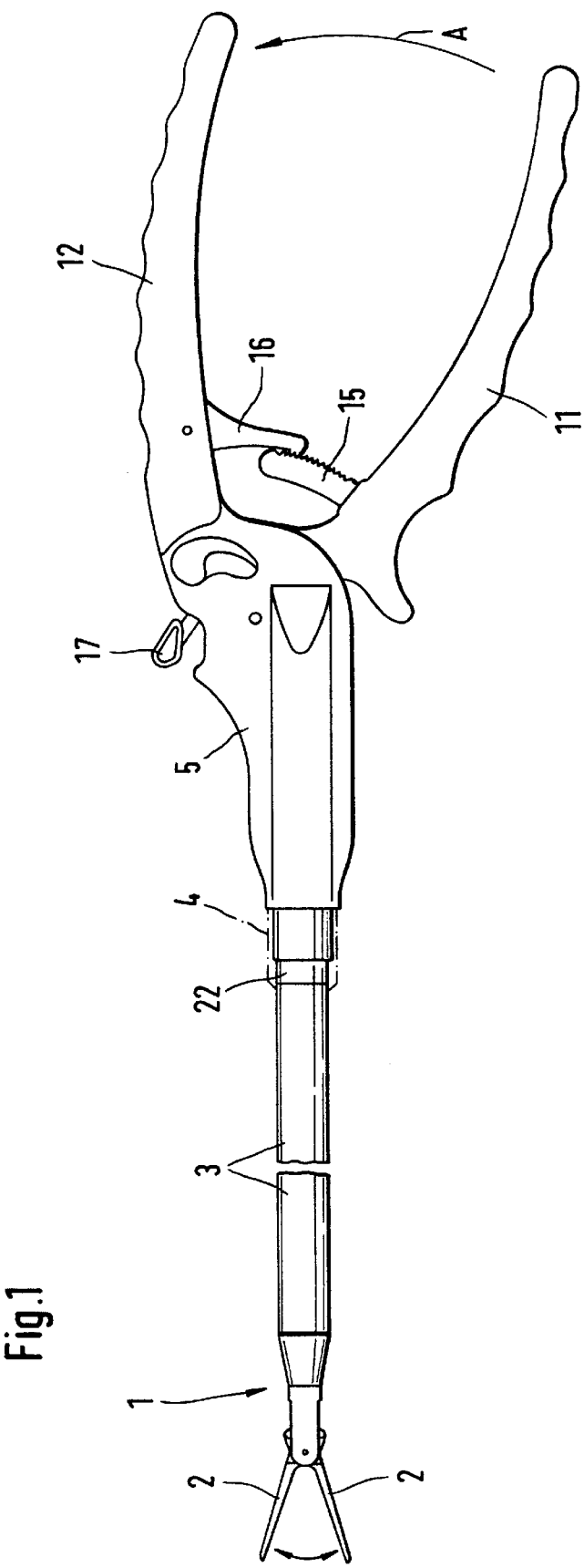
FIG. 1 a lateral view of an instrument with an opened forceps tool.

With the instrument according to FIG. 1, a forceps insert consisting of two forceps jaw parts 2 and a shank 3 connected thereto is releasably connectable at its proximal end to an instrument housing 5 of a forceps handle by way of a screw cap 4. The forceps handle comprises a pivotingly movable handle arm 11 and a handle arm 12 rigidly arranged on the housing 5. For closing the forceps jaw 4 it is necessary to pivot the pivotingly movable handle arm 11 in the direction of the rigidly arranged handle arm 12 (arrow A), wherein this pivoting movement by way of an actuating element not shown in FIG. 1, which runs axially through the shank, 3 is transmitted to the forceps jaw parts 2 in the known manner.

The opening or closing angle of the forceps jaw parts 2 may be set by way of a latching block consisting of a tooth latch 15 and a blocking hook 16. For releasing the latching it is necessary to actuate the lever 17 of the blocking hook 16, by which means the blocking hook 16 comes out of engagement with the tooth latch 15.

FIG. 2 shows the same medical instrument as in FIG. 1, but in the closed position of the forceps jaw 2 parts. With this the pivotingly movable handle arm 11 is pressed towards the rigid handle arm 12 and the blocking hook 16 is latched in at the end of the tooth latch 15.

The FIGS. 1 and 2 show only schematically an overload buffer 22 which is formed according to the invention as a shape body of elastic material and which is arranged within the screw cap 4 between the shank 3 and the instrument housing 5 and whose design and functioning manner are described in more detail further below by way of FIGS. 5 and 6.

In FIG. 2 it is indicated by way of arrows that when in the closed condition of the forceps jaw 2 further force is exerted onto the pivotingly movable handle arm 11 (arrow B) and this force exceeds a certain amount, the shank 3 is pressed proximally in the direction of the arrow C, wherein the overload buffer 22 formed as a rubber-elastic shape part is deformed planely and its periphery bulges out in the radial direction. This ensures that the force D exerted on an object G held between the forceps jaw parts 2 does not exceed a certain amount and damage on the forceps insert by way of overloading is avoided.

In the normal case (not in the overload case) the forceps jaw parts 2, which in FIG. 3 are shown in the closed condition, on actuation of the pivotingly movable handle arm 11 are closed by axial shifting of the actuating element 8 in the direction of the arrow E, and opened by opposite shifting of the actuating element 8 in the direction of the arrow F.

Also the two forceps jaw parts 2, which in each case arc formed in the shape of a two-armed lever, by way of a link pin 30 arc connected to one another in a pivotingly movable manner and to the distal end of the shank 3 which tapers here.

Furthermore the forceps jaw part lying below in FIG. 3, at its end lying proximally to tile first pivoting joint 30, is with one end connected in a pivotingly movable manner by a second link pin to a first link rod 34 which for its part at its other proximally lying end is pivotingly movably connected to the actuating element 8 by a third link pin 33.

Furthermore the forceps jaw part 2 lying above in FIG. 3 at the end of the arm lying proximally from the first pivoting joint 30 is connected in a pivotingly movable manner by way of a fourth link pin 32 to one end of a second link rod 35 which for its part at its proximal end is likewise connected to the actuating element 8 in a pivotingly movable manner by way of the third link pin 33.

If in the closed condition of the two forceps jaw parts 2 a proximally directed force (arrow E) is continued to be exerted by the actuating element this force is transmitted via the first pivoting joint 30 onto the shank 3 which by way of this is pressed proximally by a certain distance in the direction of arrow C and elastically deforms the buffer 22.

The pivotingly movable handle arm 11 and the rigidly arranged handle arm 12 according to FIG. 5 are modified with respect to the embodiment form shown in the FIGS. 1 and 2 in that they ale connected by a spring 14 so that for closing the forceps jaw 2 the pivotingly movable handle arm 11 is pivoted against the effect of the spring 14 in the direction of arrow B. The proximal end of the actuating element 8 is formed in the shape of a ball 9 which is applied into a receiver 10 of the pivotingly movable handle arm with a positive fit.

FIG. 6 shows in an enlarged view details of the region X of FIG. 5 enclosed by a line. The proximal end 6 of the shank 3, which is reduced in diameter, is introduced into the central bore of a sleeve 7 which is applied in the forceps housing 5 and which extends proximally over a certain length and is interspersed by the actuating element 8 operatinig the forceps jaw 2. Caused by the design of the sleeve 7 and of the bore of the forceps housing, which accomodates the sleeve 7 as well as of the screw cap 4, the shank 3 in the case of overloading is displaceable by a certain distance proximally in the direction of the arrow C.

The excess load is taken up by the already mentioned buffer 22 consisting of rubber-elastic material. This buffer 22 formed as a shape body is shaped annularly, is laid around the tapered end 6 of the shank 3 and is seated in a hollow cylindrical mounting 20 which does not completely enclose the shape body 22. At the end of the buffer 22, which lies opposite the mounting 20, as a closing element there may be arranged an annular disk. The mounting 20 comprises peripheral breaking-throughs or openings 36 whose function in the case of overloading is described hereinafter.

If the two handle arms 11, 12, after the forceps jaw parts 2 have been closed or have grasped an object G, for example as this is shown in FIG. 2, are impinged with a further force in the direction of the arrow B, the rubber buffer 22 is pressed together by the shank 3 being pressed proximally at the same time, in cooperation with the mounting 20 connected to the shank and with the oppositely lying section of the housing, and is deformed in a manner such that the buffer 22 partly exits out of the opening or openings 36 in the radial direction and therefore may elastically deform in order thus to accommodate forces in the case of overloading.

We claim:

1. A medical instrument, comprising:
   a housing;
   a shank having a proximal end and a distal end, the proximal end of the shank being connected to the housing;
   an openable and closable two-part tool provided at the distal end of the shank;
   an actuating element that runs through the housing and the shank so as to be axially shiftable for actuating the tool; and
   an elastic buffer as overload protection whereby the buffer elastically deforms to buffer an axial force overload transmitted from the actuating element onto the shank, the buffer being formed as a shaped body of elastic material arranged between the shank and the housing so that during overloading the buffer is deformed by the shank which at the same time shifts axially proximally with respect to the housing.

2. An instrument according to claim 1, wherein the tool is connected to the shank at a linkage point, the force to be taken up by the buffer during overloading being transmitted to the shank via the linkage point of the tool on the shank.

3. An instrument according to claim 1, and further comprising a sleeve-shaped mounting rigidly connected to the shank, the buffer being arranged in the mounting and the mounting being formed so as to only partly enclose the buffer.

4. An instrument according to claim 1, wherein the buffer consists of rubber-elastic material.

5. An instrument according to claim 3, wherein the buffer is formed as a cylindrical ring which surrounds the shank, the mounting being arranged to partly surround the buffer cylindrically.

6. An instrument according to claim 3, wherein the mounting has a wall with openings that run in a circumferential direction.

* * * * *